US012295866B2

(12) United States Patent
Acevedo et al.

(10) Patent No.: US 12,295,866 B2
(45) Date of Patent: May 13, 2025

(54) BIOMEDICAL FINGER ASSEMBLY FOR USE WITH CAPACITIVE PANELS

(71) Applicant: RCM Enterprise L.L.C., Olympia, WA (US)

(72) Inventors: Ana Rosa Acevedo, Olympia, WA (US); Bradley Arthur Crittenden, Olympia, WA (US); Erich Theodore Griebling, Olympia, WA (US); Rachel Adsit Lowing, Olympia, WA (US); Liam Aloysha Mooney, Olympia, WA (US); Catherine Rocille Treadwell, Olympia, WA (US)

(73) Assignee: RCM Enterprise L.L.C., Olympia, WA (US)

(*) Notice: Subject to any disclaimer, the term of this patent is extended or adjusted under 35 U.S.C. 154(b) by 202 days.

(21) Appl. No.: 17/221,722

(22) Filed: Apr. 2, 2021

(65) Prior Publication Data
US 2022/0313456 A1    Oct. 6, 2022

(51) Int. Cl.
*A61F 2/54* (2006.01)
*A61F 2/50* (2006.01)
*A61F 2/58* (2006.01)
*A61F 2/70* (2006.01)
*G06F 3/044* (2006.01)

(52) U.S. Cl.
CPC ............ *A61F 2/586* (2013.01); *A61F 2/5044* (2013.01); *A61F 2/588* (2013.01); *A61F 2/70* (2013.01); *G06F 3/0445* (2019.05); *A61F 2002/5001* (2013.01); *A61F 2002/5038* (2013.01);

(Continued)

(58) Field of Classification Search
None
See application file for complete search history.

(56) References Cited

U.S. PATENT DOCUMENTS

| 9,999,522 B2 | 6/2018 | Gill |
| 11,083,600 B2 | 8/2021 | Gill |

(Continued)

FOREIGN PATENT DOCUMENTS

| CN | 204274728 U | 4/2015 |
| CN | 106038009 B | 2/2018 |

(Continued)

OTHER PUBLICATIONS

International Search Report and Written Opinion dated Jul. 21, 2021 for International Application No. PCT/US2021/026909, 15 pages.

(Continued)

*Primary Examiner* — David H Willse
(74) *Attorney, Agent, or Firm* — Perkins Coie LLP

(57) ABSTRACT

A prosthetic digit usable with capacitive panels is provided. The digit includes at least one conductive layer surrounding the body of the digit, and a non-conductive sealing layer around the conductive layer preventing direct external contact of the conductive layer with the capacitive panel. The digit may have a conductive tip pad to create a series capacitive pathway between the conductive layer of the body and the electrodes of the capacitive panel. Using the digit with a capacitive panel does not require a direct conductive pathway, e.g., a pathway between the capacitive panel and the structure of the device, the user's skin, or metallic sink.

21 Claims, 6 Drawing Sheets

(52) U.S. Cl.
CPC .......... *A61F 2002/5056* (2013.01); *A61F 2002/5081* (2013.01); *G06F 2203/04103* (2013.01)

(56) References Cited

U.S. PATENT DOCUMENTS

| | | |
|---|---|---|
| 2005/0021154 A1 | 1/2005 | Brimalm |
| 2006/0212129 A1 | 9/2006 | Lake et al. |
| 2009/0096746 A1 | 4/2009 | Kruse et al. |
| 2012/0109337 A1 | 5/2012 | Schulz |
| 2012/0303136 A1 | 11/2012 | Macduff |
| 2012/0308806 A1 | 12/2012 | Leto et al. |
| 2013/0041476 A1 | 2/2013 | Schulz |
| 2013/0127791 A1 | 5/2013 | Siuta |
| 2014/0107805 A1 | 4/2014 | Varley |
| 2014/0303750 A1 | 10/2014 | MacDuff |
| 2015/0190245 A1 | 7/2015 | McLeary et al. |
| 2015/0230941 A1 | 8/2015 | Jury |
| 2016/0015100 A1 | 1/2016 | Leto |
| 2016/0224138 A1 | 8/2016 | Adkins |
| 2016/0367383 A1 | 12/2016 | Sensinger et al. |
| 2017/0007424 A1* | 1/2017 | Gill .............. A61F 2/586 |
| 2017/0020691 A1 | 1/2017 | Thompson et al. |
| 2017/0056208 A1 | 3/2017 | Thompson et al. |
| 2018/0036145 A1 | 2/2018 | Jury et al. |
| 2018/0064563 A1 | 3/2018 | Gill |
| 2018/0110631 A1 | 4/2018 | Cazenave |
| 2018/0235293 A1* | 8/2018 | Lee .................. B32B 25/20 |
| 2018/0296369 A1 | 10/2018 | Smit et al. |
| 2019/0328550 A1 | 10/2019 | Akhtar et al. |
| 2019/0374353 A1 | 12/2019 | Schulz |
| 2020/0054464 A1 | 2/2020 | Sensinger et al. |
| 2020/0060361 A1* | 2/2020 | Depriest .......... A41D 19/0024 |
| 2021/0085490 A1 | 3/2021 | Griebling et al. |
| 2021/0293643 A1 | 9/2021 | Correll et al. |
| 2021/0361445 A1 | 11/2021 | Griebling et al. |
| 2022/0133509 A1 | 5/2022 | Segil et al. |
| 2023/0320873 A1 | 10/2023 | Griebling et al. |
| 2024/0390164 A1 | 11/2024 | Griebling et al. |

FOREIGN PATENT DOCUMENTS

| | | | |
|---|---|---|---|
| CN | 109381285 A | 2/2019 | |
| DE | 23 29 929 A1 * | 1/1975 | .......... A61F 2/80 |
| DE | 102017005761 B4 | 2/2020 | |
| EP | 3110372 B1 | 1/2018 | |
| EP | 3842015 A2 | 6/2021 | |
| EP | 3856088 B1 | 8/2022 | |
| FR | 2277569 A2 | 2/1976 | |
| GB | 145267 A | 7/1920 | |
| JP | 2015146998 A | 8/2015 | |
| WO | 2010018358 A2 | 2/2010 | |
| WO | 2016187133 A1 | 11/2016 | |
| WO | 2017061879 A1 | 4/2017 | |
| WO | 2021061681 A1 | 4/2021 | |
| WO | 2021236370 A1 | 11/2021 | |
| WO | 2022211824 A1 | 10/2022 | |
| WO | 2023080796 A1 | 5/2023 | |

OTHER PUBLICATIONS

International Search Report and Written Opinion from International Application No. PCT/US2021/031637, dated Sep. 10, 2021.
ISA, International Search Report, PCT Application No. PCT/2020/052066, mailed Dec. 10, 2020.
Segil, Jacob L. et al. "The Point Digit: Mechanical Design and Testing of a Ratcheting Prosthetic Finger," Abstract, 41st Annual Meeting of the American Society of Biomechanics, Boulder CO, Aug. 8-11, 2017, 2 pages.
Ventimiglia, Paul. Major Qualifying Project submitted to Faculty of Worchester Polytechnic Institute, "Design of a Human Hand Prosthesis," Apr. 26, 2012, 75 pages.
Extended Supplementary Search Report from EP Application No. 20869041.2, dated Sep. 8, 2023.
Japanese Application No. 2022-517781 Office Action Mailed May 20, 2024.
U.S. Appl. No. 17/346,126 Final Office Action mailed Aug. 5, 2024.
U.S. Appl. No. 17/346,126, Non-Final Office Action Mailed Jan. 9, 2024, pp. 1-25.
U.S. Appl. No. 17/316,357 Final Office Action Mailed Jul. 24, 2024, pp. 1-22.
U.S. Appl. No. 18/078,693 Final Office Action Mailed Sep. 16, 2024, pp. 1-8.
U.S. Appl. No. 18/078,693, Non-Final Office Action Mailed Mar. 26, 2024, pp. 1-6.
Extended European Search Report from European Application No. 21809498.5, dated May 31, 2024, pp. 1-10.
U.S. Appl. No. 17/316,357 Non-Final Office Action Mailed May 17, 2023, pp. 1-19.
U.S. Appl. No. 17/316,357, Non-Final Office Action Mailed Jan. 23, 2024, pp. 1-19.
International Search Report from PCT Application No. PCT/US2024/031109, dated Aug. 23, 2024.
U.S. Appl. No. 17/316,357, Non-Final Office Action Mailed Jun. 23, 2022.
Extended European Search Report from European Application No. 21935405, dated Jan. 15, 2025.

* cited by examiner

BIOMEDICAL FINGER ASSEMBLY FOR USE WITH CAPACITIVE PANELS

TECHNICAL FIELD

The present technology generally relates to a finger or thumb prosthesis compatible for use with capacitive panels and, more particularly, for use with capacitive touchscreens.

BACKGROUND

Partial hand loss is the most common upper extremity amputation and has historically been underserved by conventional treatment. Most partial hand amputations are traumatic in origin, and many amputations occur in workplaces where manual labor is performed. Partial hand loss alters the ability to perform important tasks, such as sorting mail, playing an instrument, returning to a vocation, and using electronic devices. Among other difficulties, amputees who wear prosthetic digits can experience limitations in operation of consumer and commercial capacitive panel devices when the prosthesis does not include compatibility with capacitive touchscreens.

Normal operation of a capacitive panel (e.g., the touchscreen of a smartphone) requires a finger or an object to alter the capacitance at the point of contact with the touchscreen. Projected capacitive touchscreen technology (PCT) is an industry standard for gaming, signage, and mobile devices such as smartphones. PCT can operate based on mutual or self-capacitance paradigms, which detect touch by sensing the capacitive load of a finger or device when it comes into proximity of the screen. The grid of electrodes of the PCT then sends signals to software to detect finger location.

Upper extremity prosthetic digits can be formed from metallic structural portions and covered with a silicone glove or plastic fairings. The coverings can appear as skin, protect underlying electronics, renew high-wear surfaces by replacement, and improve grip during object handling. Conventional metallic structural prosthetic digits typically use a continuous conductive pathway from the point of contact to the metallic structure (or other component, such as a motor housing) to operate a capacitive panel. Other conventional prosthetic digits can be configured to operate capacitive panels by including a direct conductive pathway from the interfacing prosthetic fingertip to the skin of the user (i.e., using the skin as the capacitive sink). Forming a direct pathway has several limitations, including increased manufacturing complexity and difficulty in maintaining the conductive path through articulating joints.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

A. Overview

Figure 1A:
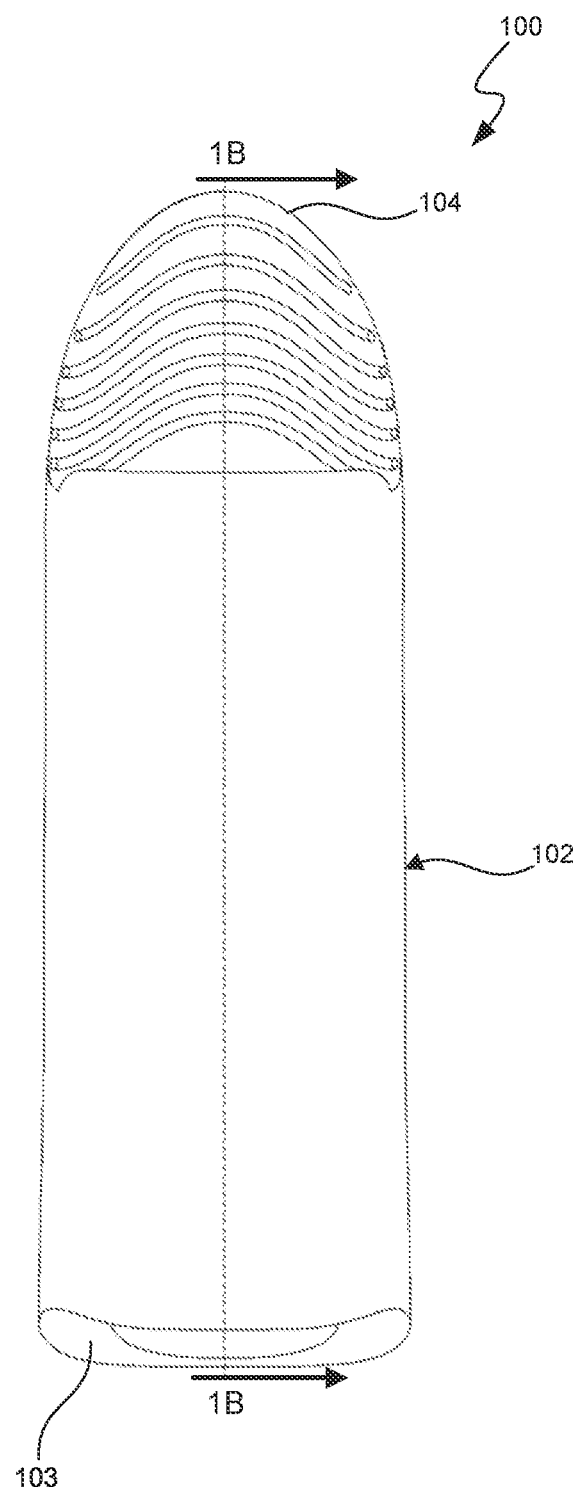
FIG. 1A shows a plan view of a prosthetic digit configured in accordance with an embodiment of the present technology.

The present technology is directed to a prosthetic digit that enables use of capacitive panel control interfaces, such as touchscreens on various consumer and commercial electronic devices (e.g., smartphones, tablets, laptops, printers, machinery, etc.). Among other uses, the capacitive panel enabled prosthetic digit configured in accordance with the present technology is configured to provide usability of an electronic device having a capacitive panel when worn as a prosthetic thumb or finger by including one or more series coupled capacitors to alter the capacitance at the point of contact with the panel.

It is desirable for prosthetic digits to be lightweight, compact, strong, and to incorporate natural joint movement. In lightweight prostheses, or prostheses with one or more articulation points, adding a direct conductive pathway between a capacitive sink and the prosthetic fingertip can increase complexity and decrease reliability of the conductive pathway. Further, while adding a heavy metallic sink can provide an endpoint for the conductive pathway, the metallic sink can interfere with use of the prosthesis by increasing the weight of the device. Digits configured in accordance with the present technology can restore the ability to operate capacitive panels by providing a lightweight digit having a capacitively coupled pathway confined within the digit, without needing to form a conductive pathway to an internal metallic structure or the skin of the user. Given increasingly prolific capacitive panel integration in consumer and commercial electronics, the ability to operate such panels is expected to increase independence in daily activities and restore related portions of vocational efficiency.

The digits disclosed herein for use with a capacitive panel generally include at least one conductive layer surrounding the body of the respective digit and a non-conductive sealing layer around the conductive layer preventing direct contact with the conductive layer. The digit may include a conductive tip pad in a series capacitive pathway between the conductive layer of the body and the electrodes of the capacitive panel to aid in capacitive coupling between the touchscreen and the conductive layer. The conductive tip pad may be configured to interact with the capacitive panel similarly to a user's intact fingertip. The digits of the present technology do not require a direct conductive pathway, e.g., a pathway to the skin of the user or to a heavy metallic sink.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims, but are not described in detail with respect to FIGS. 1 and 2.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

B. Selected Embodiments of Prosthetic Digits Compatible for Use with Capacitive Panels FIG. 1A shows a plan view of a prosthetic digit 100 ("digit 100") configured in accordance with an embodiment of the present technology. The digit 100 is configured to allow a user to control a capacitive panel (not shown) by contact of the digit 100 to the panel through series capacitive coupling. The digit 100 includes a body 102 having a proximal end portion 103 and a distal end portion 104. The body 102 may include a mounting feature (not shown) formed from a biocompatible material at the proximal end portion 103 for suspending the digit 100 from the residuum of the user, e.g., a socket (partial, radial, etc.), frame, strap, or any other suitable mounting feature. The mounting feature can be configured to secure the digit 100 to the remaining residuum in the approximate position of anatomic digits of the user. In some embodiments, it is possible to mount the digit 100 in a fashion that is non-anatomic, such as in the case of unique clinical presentations.

Figure 1B:
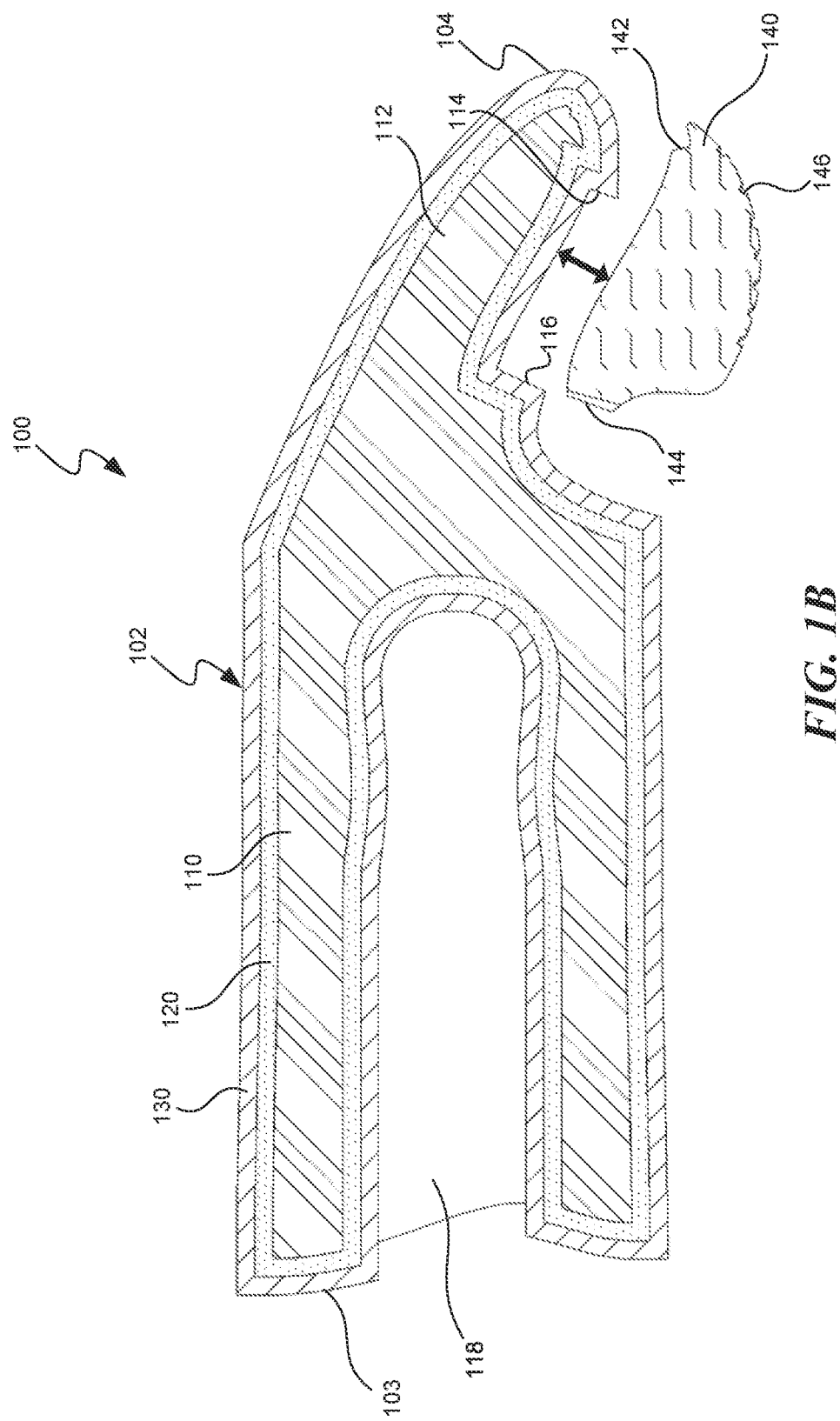
FIG. 1B shows a cross-sectional side view of the prosthetic digit of FIG. 1A, sectioned along the line 1B-1B shown in FIG. 1A.

FIG. 1B shows a cross-sectional side view of the digit 100 sectioned along the line 1B-1B in FIG. 1A. As shown, the body 102 may have a cylindrical proximal body portion 110 surrounding an inner cavity 118 and a distal body portion 112. The body 102 can be formed from a suitable lightweight material, such as plastic, carbon fiber, titanium, etc. The digit 100 includes a conductive layer 120 disposed on an outer surface of the body 102, the inner cavity 118, and a proximal-facing portion of the body 102. The conductive layer 120 generally forms a conductive shell around the proximal and distal body portions 110 and 112 of the body 102, which forms the capacitive body configured to change the capacitance at the capacitive panel. The conductive layer 120 can be formed from a suitable conducting material, e.g., a plating, a film, a paint, a primer, an adhesive, a vapor deposition coating (e.g., copper and a non-toxic material), an ink, etc.

To create the series capacitive pathway, the conductive layer 120 can be insulated from other conductive objects and the body of the user. In this regard, the digit 100 further includes an insulating layer 130 applied over the conductive layer 120. The insulating layer 130 is applied to fully surround and insulate the conductive layer 120, creating a capacitive body. The insulating layer 130 can be applied as a single layer/coat or as multiple layers/coats. In some embodiments, the insulating layer 130 is formed from an insulating primer and an insulating paint. In other embodiments, however, the insulating layer 130 is formed from any suitable insulating material, such as rubber, silicone, plastic, paint, etc., or processes such as anodizing. The digit 100 may be further covered with fairings to provide a silicone interface with objects for improved grip and allow the user to select designs and colors, or to replace these cosmetic pieces when wear occurs.

The digit 100 may include a conductive distal tip portion 140 positioned and configured to interface with the capacitive panel during use. For purposes of illustration, the conductive tip 140 is shown removably detached (see arrows) adjacent to the distal end portion 104 of the digit 100. The conductive distal tip portion 140 may be operably coupled to the digit 100 with a suitable attachment feature. In the illustrated embodiment, for example, the conductive distal tip portion 140 includes a first attachment portion 142 configured to interface with (a) a first receiving portion 114 arranged nearer the distal end portion 104, and (b) a second attachment portion 144 configured to interface with a second receiving portion 116. The first and second attachment portions 142 and 144 may be non-conductively coupled to the first and second receiving portions 114 and 116, respectively, using any suitable method, such as interference fit, fasteners, non-conductive adhesive, etc. The conductive distal tip portion 140 further comprises a plurality of grip indentations 146 formed on an interfacing surface of the conductive distal tip portion 140. Such features are expected to improve object handling for the user of the digit 100. In other embodiments, the grip indentations 146 may have a different arrangement/pattern. The conductive distal tip portion 140 may be formed from a conductive material, such as conductive silicone (e.g., silicone having conductive filler), elastomer, polymer, film, paper, fabric, metal, or other suitable conductive materials.

The conductive distal tip portion 140 is configured to bridge the distance between a capacitive panel (not shown) and the conductive layers 120 to form the series capacitive pathway/coupling. Capacitive coupling (e.g., electric field or electrostatic coupling) does not require contact between the capacitive panel and the capacitive body (e.g., the conductive layer 120) for use of the capacitive panel. In this regard, the conductive distal tip portion 140 is not in direct electrical communication with the conductive layer 120. As is known to those of skill in the art, capacitance between the two objects is a function of the surface area of the objects, the distance between the objects, and the permittivity (i.e., the ability of a substance to store electrical energy in an electric field). A threshold capacitance value can mimic the human body to operate the capacitive panel. In some embodiments, the capacitive series between the conductive layer 120, the distal tip portion 140, and the capacitive panel provides a threshold capacitance value to operate the capacitive panel. In other embodiments, the digit 100 may be used with the capacitive panel without the conductive distal tip portion 140, such as in embodiments where the distance between the conductive layer 120 and the capacitive panel is relatively short. Other configurations are also within the scope of the present disclosure.

Referring to FIGS. 1A and 1B together, a method of manufacturing the digit 100 for use with a capacitive panel in accordance with embodiments of the present technology may include obtaining the body 102 and applying the conductive layer 120 to surfaces of the body 102 to at least partially surround the body 102. The method then includes and applying the insulating layer 130 atop the conductive layer 120, such that the conductive layer is insulated and not exposed for external conductive electrical contact. The conductive layer 120 may be configured to alter the capacitance of the capacitive panel when the body 102 is in proximity to the capacitive panel. The method of manufacturing may further include operably coupling the conductive distal tip portion 140 to the distal end portion 104 of the body 102 such that the conductive distal tip portion 140 is insulated from the conductive layer 120. The conductive distal tip portion 140 is configured to contact the capacitive panel during use.

Figure 2A:
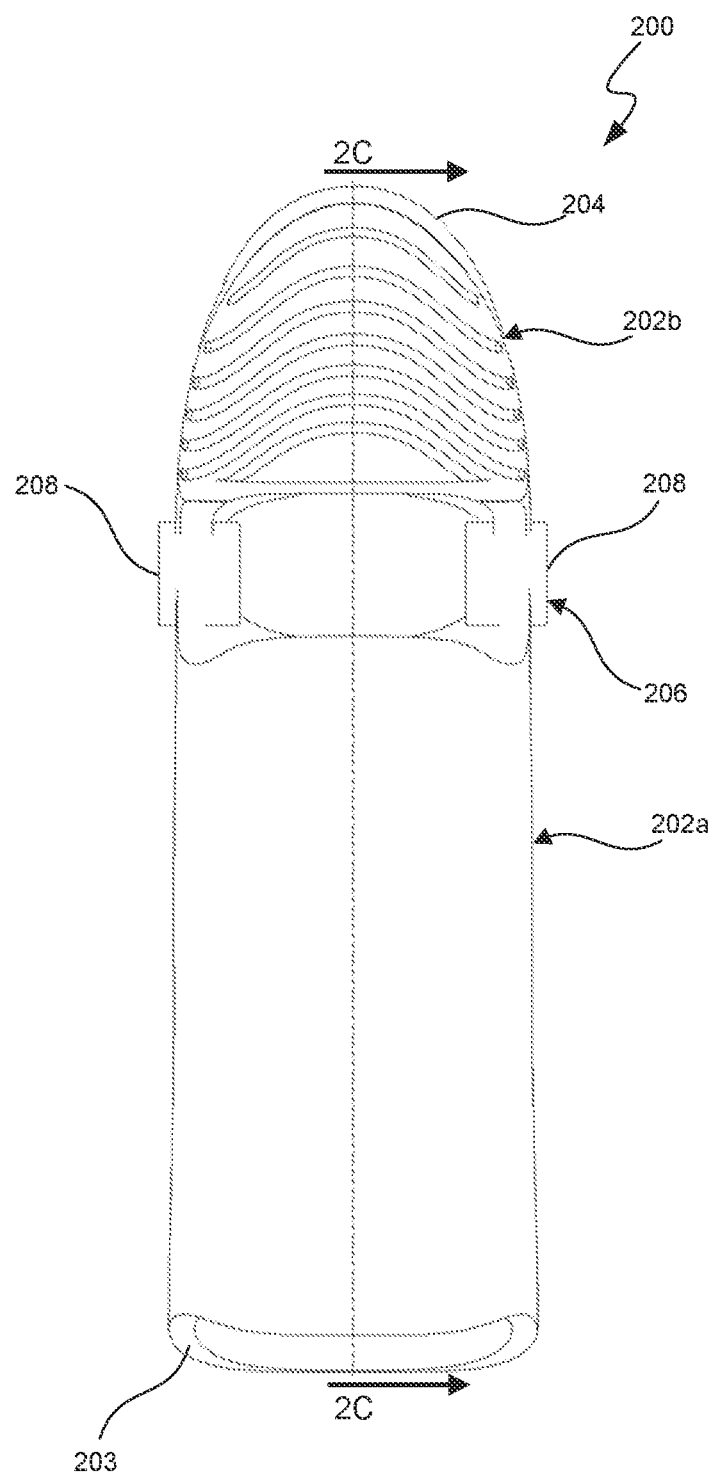
FIGS. 2A and 2B show plan and side views, respectively, of a prosthetic digit configured in accordance with an embodiment of the present technology.
Figure 2B:
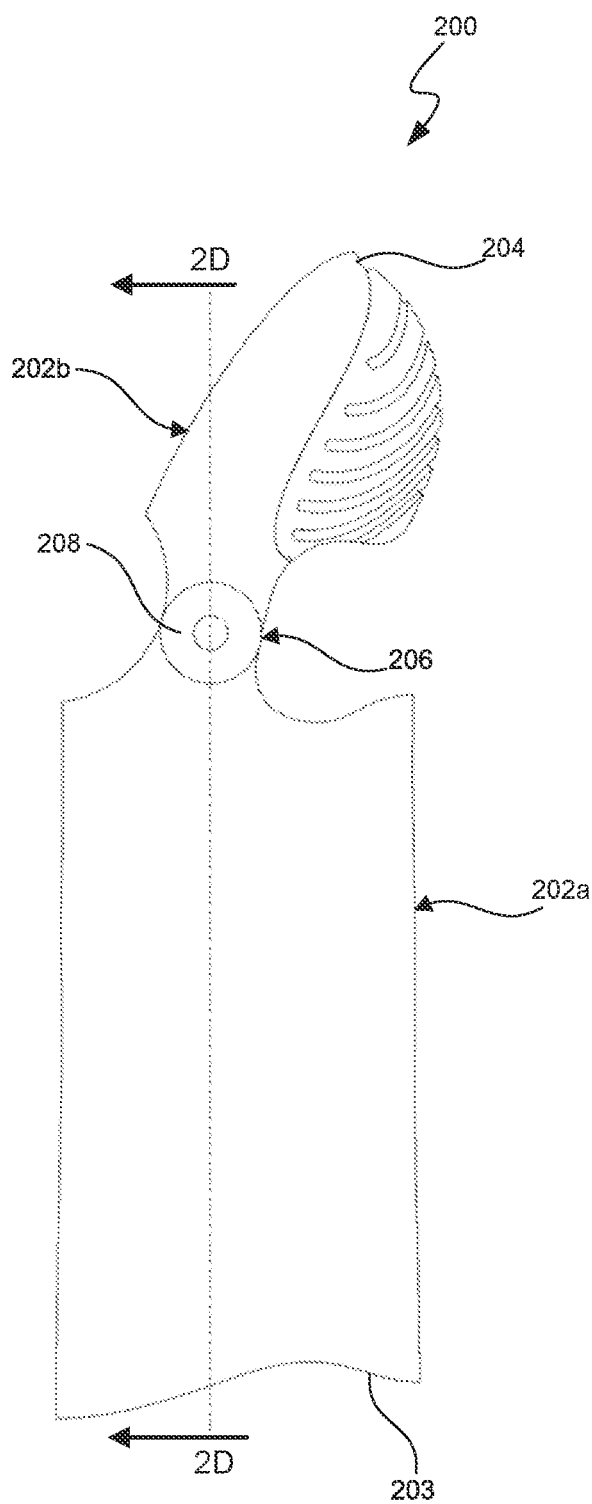

FIGS. 2A and 2B show plan and side views, respectively, of a prosthetic digit 200 ("digit 200") configured in accordance with an embodiment of the present technology. The digit 200 is similar to the digit 100 of FIGS. 1A and 1B, except that the digit 200 shows a variation having an articulable joint. Like reference numbers to the embodiments of FIGS. 1A and 1B refer to similar features in FIGS. 2A-2D, but are listed in the 200-series and may have variations and/or have different shapes and sizes.

The digit 200 is configured to allow a user to control a capacitive panel (not shown) by contact of the digit 200 to the panel through capacitive coupling. The digit 200 includes a proximal body portion 202a having a proximal end portion 203, a distal body portion 202b having a distal end portion 204, and an articulating joint 206 therebetween. The articulating joint 206 includes a joint hinge 208. The proximal and distal body portions 202a and 202b may generally represent bones of the finger, with the articulating joint 206 generally representing the distal interphalangeal (DIP) joint.

The proximal body portion 202a may include a mounting feature (not shown) formed from a biocompatible material at the proximal end portion 203 for suspending the digit 200 from the residuum of the user, e.g., a socket (partial, radial, etc.), frame, strap, or any other suitable mounting feature. The mounting feature can be configured to secure the digit 200 to the remaining residuum in the approximate position of anatomic digits of the user. In some embodiments, it is possible to mount the digit 200 in a fashion that is non-anatomic, such as in the case of unique clinical presentations.

Figure 2C:
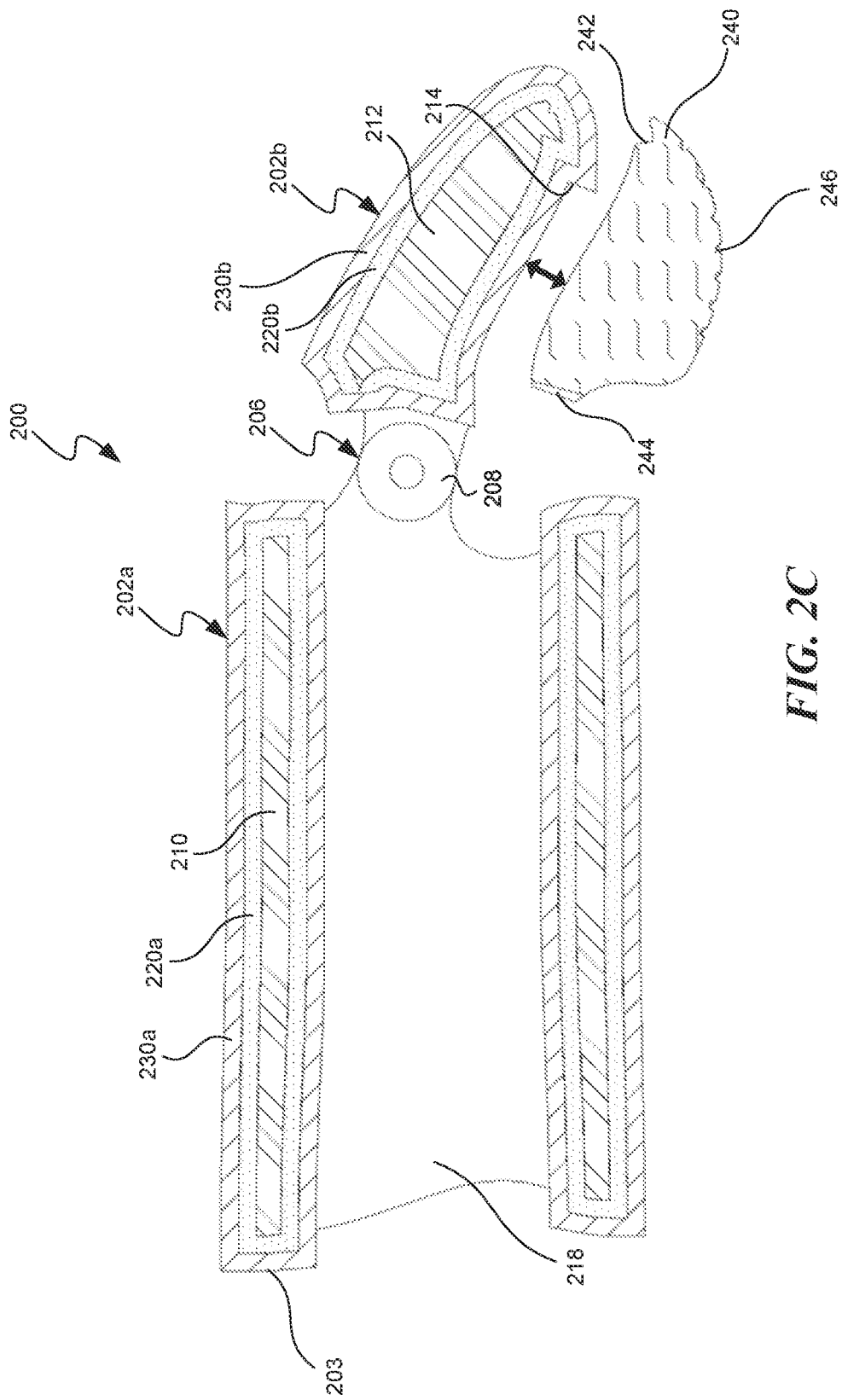
FIG. 2C shows a cross-sectional side view of the prosthetic digit of FIGS. 2A and 2B, sectioned along the line 2C-2C shown in FIG. 2A.
Figure 2D:
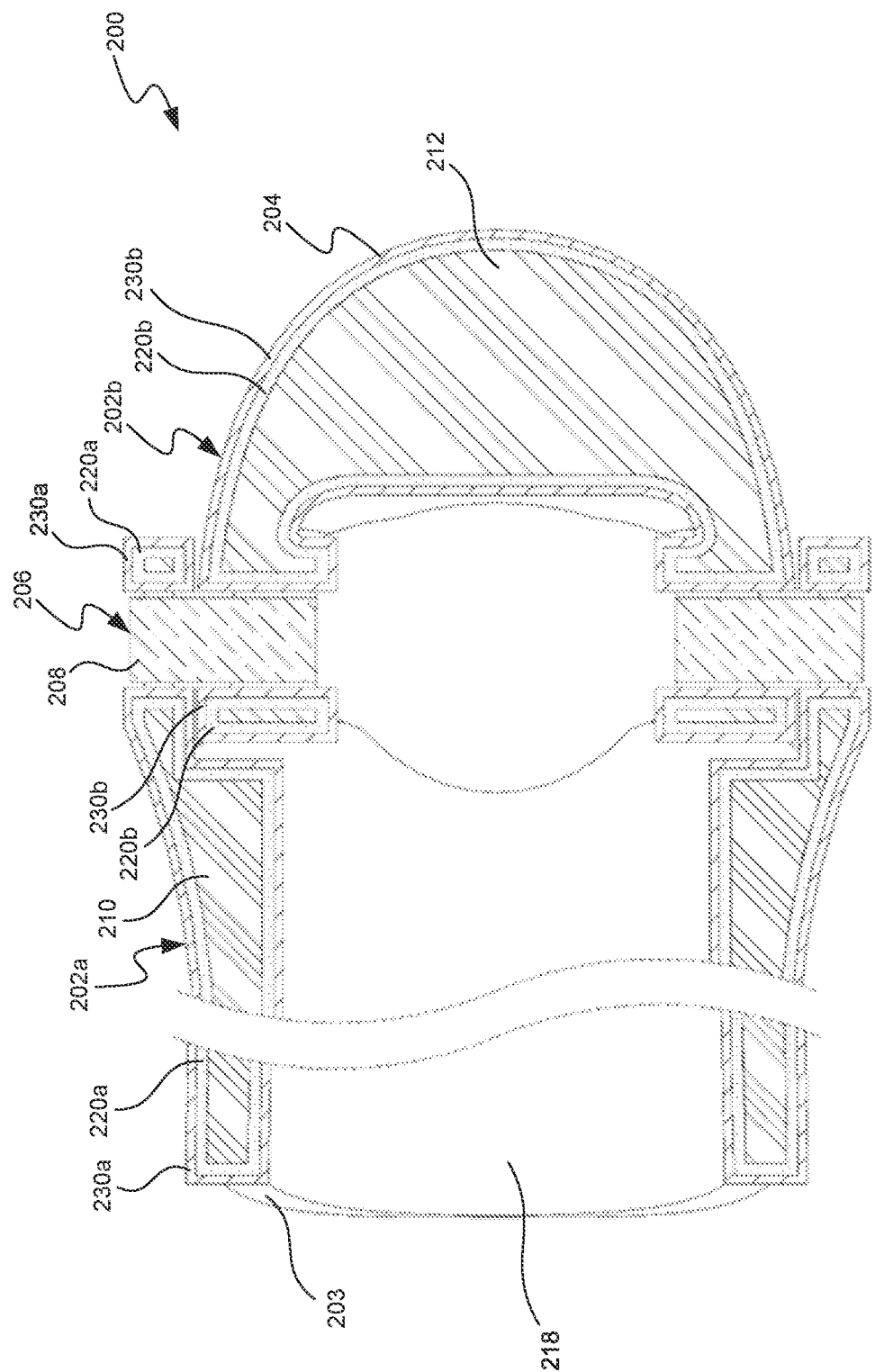
FIG. 2D shows a cross-sectional plan view of the prosthetic digit of FIGS. 2A and 2B, sectioned along the line 2D-2D shown in FIG. 2B.

FIG. 2C shows a cross-sectional side view of the digit 200 sectioned along the line 2C-2C in FIG. 2A, and FIG. 2D shows a cross-sectional plan view of the digit 200 sectioned along the line 2D-2D in FIG. 2B. As shown, the proximal body portion 202a may have a cylindrical proximal body 210 surrounding an inner cavity 218. The proximal body 210 can be formed from a suitable lightweight material, such as plastic, carbon fiber, titanium, etc. The distal body portion 202b may have a distal body 212 that is articulable through the articulating joint 206 with respect to the proximal body 210. The distal body 212 can be formed from the same material as the proximal body 210, or from a different suitable lightweight material.

The digit 200 includes a proximal conductive layer 220a disposed on an outer surface of the proximal body 210, the inner cavity 218, and a proximal-facing portion of the proximal body 210. Similarly, the digit 200 includes a distal conductive layer 220b disposed on an outer surface of the distal body 212. The proximal and distal conductive layers 220a and 220b generally form a conductive shell around the proximal and distal bodies 210 and 212, respectively, which form a series of capacitive bodies configured to change the capacitance at the capacitive panel. The proximal and distal conductive layers 220a and 220b can be formed from a suitable conducting material, e.g., a plating, a film, a paint, a primer, an adhesive, a vapor deposition coating (e.g., copper and a non-toxic material), an ink, etc.

To create the series capacitive pathway, the proximal and distal conductive layers 220a and 220b can be insulated from each other, from other conductive objects, and from the body of the user. In this regard, the digit 200 further includes a proximal insulating layer 230a applied over the proximal conductive layer 220a around the inner cavity 218 and the proximal-facing portion of the proximal body 210. Similarly, the digit 200 includes a distal insulating layer 230b applied over the distal conductive layer 220b around the outer surface of the distal body 212. The proximal and distal insulating layers 230a and 230b are applied to fully surround and insulate the proximal and distal conductive layers 220a and 220b. The proximal and distal insulating layers 230a and 230b can be applied as a single layer/coat or as multiple layers/coats. In some embodiments, the proximal and distal insulating layers 230a and 230b are formed from an insulating primer and an insulating paint. In other embodiments, however, the proximal and distal insulating layers 230a and 230b are formed from any suitable insulating material, such as rubber, silicone, plastic, paint, etc., or processes such as anodizing. The digit 200 may be further covered with fairings to provide a silicone interface with objects for improved grip and allow the user to select designs and colors, or to replace these cosmetic pieces when wear occurs.

The digit 200 may include a conductive distal tip portion 240 positioned and configured to interface with the capacitive panel during use. For purposes of illustration, the conductive tip 240 is shown removably detached (see arrows) from the distal body portion 202b of the digit 200. The conductive distal tip portion 240 may be operably coupled to the digit 200 with a suitable attachment feature. In the illustrated embodiment, for example, the conductive distal tip portion 240 includes a first attachment portion 242 configured to interface with (a) a first receiving portion 214 arranged nearer the distal end portion 204, and (b) a second attachment portion 244 configured to interface with a second receiving portion (not shown, see, e.g., the second receiving portion 116 of FIG. 1B) arranged near a proximal end of the distal body portion 202b. The first and second attachment portions 242 and 244 may be non-conductively coupled to the distal body portion 202b, using any suitable method, such as interference fit, fasteners, non-conductive adhesive, etc. The conductive distal tip portion 240 further comprises a plurality of grip indentations 246 formed on an interfacing surface of the conductive distal tip portion 240. Such features are expected to improve object handling for the user of the digit 200. In other embodiments, the grip indentations 246 may have a different arrangement/pattern. The conductive distal tip portion 240 may be formed from a conductive material, such as conductive silicone (e.g., silicone having conductive filler), elastomer, polymer, film, paper, fabric, metal, or other suitable conductive materials.

The conductive distal tip portion 240 is configured to bridge the distance between a capacitive panel (not shown) and the distal conductive layer 220b to form the series capacitive pathway/coupling between the capacitive panel and the distal conductive coating 220b. Capacitive coupling (e.g., electric field or electrostatic coupling) does not require contact between the capacitive panel and the capacitive body or bodies (e.g., the proximal and distal conductive layers 220a and 220b are nearly spaced in areas around the articulating joint 206) for use of the capacitive panel. In this regard, the conductive distal tip portion 240 is not in direct electrical communication with the proximal and distal conductive layers 220a and 220b. As is known to those of skill in art, capacitance between the two objects is a function of the surface area of the objects, the distance between the objects, and the permittivity (i.e., the ability of a substance to store electrical energy in an electric field). A threshold capacitance value can mimic the human body to operate the capacitive panel. In some embodiments, the capacitive series between the proximal and distal conductive layers 220a and 220b, the conductive distal tip portion 240, and the capacitive panel provides a threshold capacitance value to operate the capacitive panel. In other embodiments, the digit 200 may be used with the capacitive panel without the conductive distal tip portion 240, such as embodiments where the distance between distal conductive layers 220b and the capacitive panel is relatively short. Other configurations are also within the scope of the present disclosure.

Referring to FIGS. 2A-2D together, a method of manufacturing the digit 200 for use with a capacitive panel in accordance with embodiments of the present technology may include obtaining the proximal body 210 and the distal body 212 and pivotably coupling the proximal body 210 to the distal body 212 at the articulating joint 206. The method can further include applying the proximal and distal conductive layers 220a and 220b to surfaces of the proximal and distal bodies 210 and 212, respectively, to at least partially surround the proximal and distal bodies 210 and 212. The method then includes applying proximal and distal insulating layers 230a and 230b atop the first and second conductive layers 220a and 220b, respectively, such that the conductive layers are insulated and not exposed for external conductive electrical contact. The proximal and distal conductive layers 220a and 220b may be configured to alter the capacitance of the capacitive panel when the distal body 212 is in proximity to the capacitive panel. The method of manufacturing may further include operably coupling the conductive distal tip portion 240 to the distal body 212 such that the conductive distal tip portion 240 is insulated from the proximal and distal conductive layers 220a and 220b. The conductive distal tip portion 240 is configured to contact the capacitive panel during use.

C. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while the conductive layer is shown in the embodiment of FIGS. 2A-2D on both the proximal body and the distal body, in other embodiments the conductive layer may be disposed on only one of the proximal body or distal body, or the conductive layer may be disposed on both the proximal body and the distal body, but the proximal body may omit the insulating layer atop the conductive layer, or may be an uninsulated metallic strut. While steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A prosthetic digit for use with a capacitive panel, the prosthetic digit comprising:
   a body having a proximal end portion and a distal end portion, wherein the body is configured to replace a portion of a natural digit, and wherein the body is removably couplable to a residuum of a user at the proximal end portion;
   a conductive layer at least partially covering the body;
   an insulating layer encapsulating the conductive layer; and
   a conductive tip removably couplable to the distal end portion of the body, wherein the conductive tip is configured to interface with the capacitive panel during use,
   wherein, when the conductive tip is in proximity to the capacitive panel, a series capacitive pathway from the conductive tip to the conductive layer alters the capacitance of the capacitive panel.

2. The prosthetic digit of claim 1, wherein:
   the body comprises a proximal body portion and a distal body portion pivotably coupled to the proximal body portion;
   the conductive layer comprises a first conductive layer disposed on the distal body portion;
   the insulating layer comprises a first insulating layer; and
   the prosthetic digit further comprises—
      a second conductive layer disposed on and at least partially covering the proximal body portion; and
      a second insulating layer encapsulating the second conductive layer and electrically insulating the second conductive layer from the first conductive layer.

3. The prosthetic digit of claim 1, wherein the conductive tip is electrically insulated from the conductive layer.

4. The prosthetic digit of claim 1, wherein the conductive tip comprises a conductive silicone, conductive elastomer, conductive polymer, conductive film, conductive paper, conductive fabric, or metal.

5. The prosthetic digit of claim 1, wherein a proximal body portion is substantially cylindrical and defines an inner cavity.

6. The prosthetic digit of claim 1, wherein the insulating layer comprises a non-conductive primer layer and a non-conductive paint layer atop the non-conductive primer layer.

7. The prosthetic digit of claim 1, wherein the conductive layer comprises a conductive plating, conductive film, conductive paint, conductive primer, conductive adhesive, conductive vapor deposition coating, or conductive ink.

8. The prosthetic digit of claim 1, further comprising a fairing couplable to the body.

9. A prosthetic digit for use with a capacitive panel, the prosthetic digit comprising:
   a proximal body removably couplable to a residuum of a finger of a user;
   a distal body pivotably coupled to the proximal body, wherein the proximal body and distal body are configured to replace a portion of a natural digit;
   a first conductive layer surrounding the distal body;
   a second conductive layer surrounding the proximal body; and
   an insulating layer encapsulating one of the first or second conductive layers,
   wherein, when the distal body is in proximity to the capacitive panel, the first and second conductive layers are configured to alter the capacitance thereof.

10. The prosthetic digit of claim 9, further comprising a conductive distal tip portion operably couplable to the distal body, wherein—
   the conductive distal tip portion is insulated from the first conductive layer;
   the conductive distal tip portion is configured to interface with the capacitive panel during use; and
   a series capacitive pathway from the conductive tip to the first conductive layer alters the capacitance of the capacitive panel.

11. The prosthetic digit of claim 10, wherein the conductive distal tip portion comprises a conductive silicone, conductive elastomer, conductive polymer, conductive film, conductive paper, conductive fabric, or metal.

12. The prosthetic digit of claim 9, wherein the proximal body is substantially cylindrical and defines an inner cavity.

13. The prosthetic digit of claim 9, wherein the insulating layer comprises a first insulating layer, and wherein the prosthetic digit further comprises a second insulating layer at least partially encapsulating the other of the first or second conductive layers with respect to the first insulating layer and electrically insulating the second conductive layer from the first conductive layer.

14. The prosthetic digit of claim 9, wherein the insulating layer comprises a non-conductive primer layer and a non-conductive paint layer atop the non-conductive primer layer.

15. The prosthetic digit of claim 9, wherein the first and second conductive layers comprise a conductive plating, conductive film, conductive paint, conductive primer, conductive adhesive, conductive vapor deposition coating, or conductive ink.

16. The prosthetic digit of claim 9, further comprising a fairing couplable to the proximal and distal bodies.

17. A method of manufacturing a prosthetic digit for use with a capacitive panel, the method comprising:
   obtaining a body removably couplable to a residuum of a finger of a user, wherein the body is configured to replace a portion of a natural digit;
   applying a conductive layer to at least a portion of a surface of the body; and
   applying an insulating layer atop the conductive layer such that the conductive layer is fully surrounded by the insulating layer and not exposed for conductive electrical contact with the capacitive panel,
   wherein the conductive layer is configured to alter the capacitance of the capacitive panel when the body is in proximity to the capacitive panel.

18. The method of claim 17, further comprising operably coupling a conductive distal tip to the body, wherein the conductive distal tip is insulated from the conductive layer, and wherein the conductive distal tip is configured to interface with the capacitive panel during use and form a series capacitive pathway from the conductive tip to the conductive layer to alter the capacitance of the capacitive panel.

19. The method of claim 17, wherein:
   the body comprises a proximal body portion and a distal body portion pivotably coupled to the proximal body portion;
   the conductive layer comprises a first conductive layer disposed on the distal body portion;
   the insulating layer comprises a first insulating layer; and
   wherein the method further comprises—
      applying a second conductive layer to surfaces of the proximal body portion; and
      applying a second insulating layer atop the second conductive layer to electrically insulate the second conductive layer from the first conductive layer.

20. The method of claim 17, wherein applying the insulating layer comprises applying a non-conductive primer layer and then applying a non-conductive paint layer atop the non-conductive primer layer.

21. The method of claim 17, wherein the conductive layer comprises a conductive plating, conductive film, conductive paint, conductive primer, conductive adhesive, conductive vapor deposition coating, or conductive ink.

* * * * *